(12) United States Patent
Hsieh et al.

(10) Patent No.: US 10,047,039 B2
(45) Date of Patent: *Aug. 14, 2018

(54) COMPOUNDS, COMPOSITIONS AND METHODS FOR TREATING TUMORS

(71) Applicant: Chang Gung University, Tao-Yuan (TW)

(72) Inventors: Pei-Wen Hsieh, New Taipei (TW); Ching-Ping Tseng, Taoyuan (TW); Yun-Zhan Tsai, Taoyuan (TW); Yu-Ling Huang, Taichung (TW); Yao-Wen Chang, Pingtung County (TW)

(*) Notice: Subject to any disclaimer, the term of this patent is extended or adjusted under 35 U.S.C. 154(b) by 0 days.

This patent is subject to a terminal disclaimer.

(21) Appl. No.: 15/455,154

(22) Filed: Mar. 10, 2017

(65) Prior Publication Data
US 2017/0183294 A1 Jun. 29, 2017

Related U.S. Application Data

(60) Continuation-in-part of application No. 14/287,735, filed on May 27, 2014, now Pat. No. 9,604,910, which is a division of application No. 13/687,207, filed on Nov. 28, 2012, now abandoned.

(51) Int. Cl.
*C07C 237/32* (2006.01)

(52) U.S. Cl.
CPC .................. *C07C 237/32* (2013.01)

(58) Field of Classification Search
CPC .... C07C 235/34; C07C 235/84; C07C 237/32
See application file for complete search history.

(56) References Cited

U.S. PATENT DOCUMENTS

9,604,910 B2 * 3/2017 Tseng .................... C07C 233/65

* cited by examiner

*Primary Examiner* — Pancham Bakshi (57) ABSTRACT

Disclosed herein are compounds, compositions and methods for treating tumors, particularly tumors that metastasize, via inhibiting tumor cells-induced platelet aggregation. The compound of the present disclosure has the formula (I),

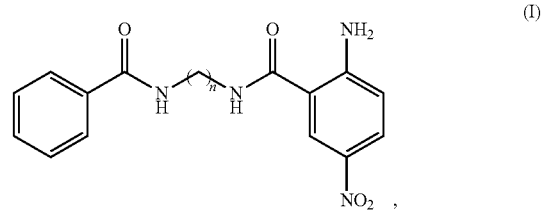

wherein, n is 2 or 3.

5 Claims, 3 Drawing Sheets

COMPOUNDS, COMPOSITIONS AND METHODS FOR TREATING TUMORS

CROSS-REFERENCES TO RELATED APPLICATIONS

This application is a continuation-in-part of U.S. patent application Ser. No. 14/287,735 filed May 27, 2014, which is a divisional application of U.S. patent application Ser. No. 13/687,207 filed Nov. 28, 2012, now abandoned, which application claims the benefit of Taiwan Patent Application No. 101124690 filed Jul. 9, 2012, in the Taiwan Intellectual Property Office; the entire contents of each of which are incorporated herein by reference.

BACKGROUND OF THE INVENTION

1. Field of Invention

The present invention relates to a 5-nitrobenzoate derivative and its use as an anti-metastatic agent for the treatment of tumors, particularly tumors that metastasize, via the inhibition of tumor cell-induced platelet aggregation (TCIPA).

2. Description of Related Arts

Tumor cells can stimulate platelet activation and form the aggregation complex with platelets in the vascular circulation system. This interaction is termed as tumor cell-induced platelet aggregation (TCIPA). The ability of tumor cells to induce platelet aggregation has been proven to highly correlate with the metastatic capability of malignant tumor. At present, it is known that there are many factors and mechanisms involved in TCIPA. For instance, tumor cells activate coagulation cascade via thrombin generation and induce platelet aggregation. Besides, adenosine diphosphate (ADP) release is involved in MCF-7 tumor cells-induced platelet aggregation that is relevant to the expression of platelet surface P2Y12 receptor (Alonso-Escolano et al., Br. J. Pharmacol. 141: 241-252, 2004). Other factors including (1) proteinases: cathepsin B and matrix metalloprotease (MMPs), (2) thromboxane A2 and prostacyclin, (3) nitric oxide (NO), (4) platelet surface proteins (e.g. GPIb-IX-V, GPIIb/IIIa and P-selectin, etc.) and so on are involved in TCIPA (Jurasz et al., Br. J. Pharmacol. 143: 819-826, 2004). Based on these results, the detail mechanism of TCIPA seems to very complicated and still be obscured. Nevertheless, these results highlight TCIPA as a target for development of cancer therapeutic strategies in translational medicine.

As so far, various approaches and anti-platelet agents have been reported to inhibit TCIPA that potentially can be used as the strategies for treatment of tumor metastasis. For example, the anti-platelet/coagulation molecule heparin can reduce the cancer-associated thromboembolism risk. In clinic, low molecular weight heparin (LMWH) is administrated to cancer patients to inhibit factor Xa and thrombin to block platelet aggregation, despite that LMWH is not tumor-specific and LMWH overdose usually increases the bleeding risk of cancer patients (Borsig, Progress in Molecular Biology and Translational Science. 93: 335-349, 2010; Lee, et al., N. Engl. J. Med. 349: 146-153, 2003). A common salicylate acid drug, aspirin, inhibits cyclooxygenase (COX) and subsequently blocks thromboxane A2 (TXA2) generation and platelet aggregation. Nevertheless, high dose aspirin does not show specificity and does not have effects on cancer metastasis and patient protection in clinics (Jurasz et al., Br. J. Pharmacol. 143: 819-826, 2004). Recently, utilizing antibody to obstruct the interaction between platelets and tumor cells serves as a promising approach to block metastasis. For example, anti-aggrus/podoplanin antibody has been used to inhibit the interaction of TCIPA between the transmembrane protein ("podoplanin") of cancer cell and C-type lectin-like receptor 2 (CLEC-2) of platelet. Antibody therapy is usually expensive and patients might suffer from the risk of autoantibody generation (Nakazawa et al., Cancer Sci. 102: 2051-2057, 2011). On the whole, the problems in the prior art lie in that the functions of platelet aggregation are still influenced such that tumor cells cannot be specifically inhibited and TCIPA is not efficiently inhibited.

In view of the above, there exists in the relevant art a need of an improved medicament that may address the above mentioned difficulty encountered in the prior art.

SUMMARY OF THE INVENTION

For overcoming the difficulty in the prior art, a series novel 5-nitrobenzoate derivatives are synthesized, these compounds do not affect platelet aggregation, yet are effective in suppressing TCIPA, specifically, the platelet aggregation induced by a surface protein-podoplanin (PDPN), of tumor cells. Therefore, the 5-nitrobenzoate derivatives of the present disclosure are suitable for use as a lead compound for the development of an anti-cancer medicament for suppressing the metastasis of tumor cells.

Accordingly, it is the first aspect of the present disclosure to provide a 5-nitrobenzoate derivative having the structure of formula I, or a pharmaceutically acceptable salt, solvate or hydrate thereof, wherein n is 2 or 3.

According to one preferred embodiment, in the compound of formula (I), n is 2.

According to embodiments of the present disclosure, the compound of formula (I) may suppress the tumor cell-induced platelet aggregation (TCIPA).

The second aspect of the present disclosure thus pertains to a pharmaceutical composition for the treatment of cancers, particularly, cancers that metastasize. The pharmaceutical composition comprises an effective amount of the compound of formula (I), and a pharmaceutically acceptable carrier.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

A further aspect of the present disclosure is to provide a method of inhibiting tumor cells-induced platelet aggregation and/or metastasis of a tumor in a subject by administrating to the subject the pharmaceutical composition of the present disclosure.

According to preferred embodiments of the present disclosure, the compound of formula (I) is administered to the subject in the amount of 0.01-100 mg/Kg.

Examples of tumors that may be treated with the present method include, but are not limited to, leukemia, Hodgkin's disease, lymphoma, Ewing's sarcoma, multiple myeloma, Wilms' tumor, bone tumor, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, skin cancers other than melanoma, and CNS neoplasm.

In all embodiments, the subject is a human.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed

BRIEF DESCRIPTION OF THE DRAWINGS

The above objectives and advantages of the present invention will become more readily apparent to those ordinarily skilled in the art after reviewing the following detailed descriptions and accompanying drawings.

DETAILED DESCRIPTION OF THE INVENTION

The detailed description provided below in connection with the appended drawings is intended as a description of the present disclosure and is not intended to represent the only forms in which the present disclosure may be constructed or utilized.

1. Definitions

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x H2O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 H2O)), and polyhydrates (x is a number greater than 1, e.g., dihydrates (R.2 H2O) and hexahydrates (R.6 H2O)).

Unless otherwise indicated, "an effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically acceptable carrier" refers to a carrier, whether diluent or excipient, that is compatible with the other ingredients of a formulation and not deleterious to the recipient thereof.

The terms "administration of a composition" or "administering a composition" is defined to include an act of providing a compound or pharmaceutical composition of the present invention to the subject in need of treatment.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Novel Compounds

The compounds as described herein can have the structure of formula (I), or a pharmaceutically acceptable salt, solvate, or hydrate thereof:

wherein n is 2 or 3.

In one preferred embodiment, in the formula (I), n is 2.

In certain embodiments, compounds of the invention are the compounds described herein, and pharmaceutically acceptable salts, solvates, or hydrates.

According to preferred embodiments of the present disclosure, the compound of formula (I) does not affect platelet aggregation, but may suppress TCIPA. Accordingly, the compound of formula (I) acts as an anti-metastasis agent thus may be useful as a lead compound for the development of a medicament suitable for the treatment of tumors, particularly, tumors that metastasize.

Any of the compounds described herein can be prepared by routine methods known in the art, or by methods presented in the working examples of the present disclosure.

3. Pharmaceutical Formulation

This invention encompasses pharmaceutical compositions for the treatment of tumors, particularly, tumors that metastasize. The pharmaceutical composition comprises a therapeutically effective amount of a compound of formula (I) of the present invention, and a pharmaceutically acceptable carrier.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

Examples of tumors that may be treated with the present pharmaceutical composition include, but are not limited to, leukemia, Hodgkin's disease, lymphoma, Ewing's sarcoma, multiple myeloma, Wilms' tumor, bone tumor, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, skin cancers other than melanoma, and CNS neoplasm.

Additionally or optionally, in some preferred embodiments, the present pharmaceutical composition may further comprise another agent to ameliorate or alleviate symptoms associated with tumors.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., $\alpha$-cyclodextrin or $\beta$-cyclodextrin), and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:corn oil).

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art.

3.1 Oral Dosage Forms

Pharmaceutical compositions of the present invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

3.2 Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: water; aqueous vehicles such as, but not limited to, sodium chloride solution, Ringer's solution, and Dextrose; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

3.3 Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition 4. Method of Use The present invention encompasses a method of inhibiting tumor cells-induced platelet aggregation and/or metastasis of a tumor in a subject. The method comprises the step of administering the present pharmaceutical composition, which comprises a therapeutically effective amount of any of the compound of formula (I) of the present disclosure, to the subject, so as to inhibit the growth or metastasis of the tumor.

Examples of tumors treatable by the present method include, but are not limited to, leukemia, Hodgkin's disease, lymphoma, Ewing's sarcoma, multiple myeloma, Wilms' tumor, bone tumor, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, skin cancers other than melanoma, and CNS neoplasm.

Accordingly, in some embodiments, the method further includes the step of administering to the subject, another agent, such as a known anti-cancer agent, before, together with, or after the administration of the present pharmaceutical composition.

The amount, route of administration and dosing schedule of the present pharmaceutical composition will depend upon factors such as the specific indication to be treated, prevented, or managed, and the age, sex and condition of the patient. The roles played by such factors are well known in the art, and may be accommodated by routine experimentation.

5. Kits

Also encompasses within the present disclosure is an article of manufacture or "kit," containing materials useful for the treatment of a tumor in a subject.

In one embodiment, the kit comprises a container comprising the compound of the present disclosure (i.e., the compound of formula (I)). The kit is suitable for the treatment of a tumor, particularly, a tumor that metastasizes. Suitable containers include, for example, bottles, vials, syringes, blister pack, and etc. The container may be formed from a variety of materials such as glass, or plastic. The contain may hold a compound of the present disclosure or a pharmaceutical formulation thereof, in an amount effective for the treatment of tumor, and may have a sterile access port, for example, the container may be an intravenous solution bag or a vail having a stopper pierceable by a hypodermic injection needle). The kit may further comprise a label or package insert on or associated with the container. The label or package insert indicates that the composition is used for treating condition of choice. Alternatively or additionally, the kit may further comprise a second container comprising a pharmaceutically acceptable buffer, such as a phosphate-buffered saline, Ringer's solution or dextrose solution. It may further include other materials desirable from a commercial and user standpoint, including other buffers, diluents, filters, needles, and syringes.

The kit may further include directions for the administration of the compound of the present invention and, if present, the second formulation for treating tumors. For example, if the kit comprises a first composition comprising the compound of the present disclosure, and a second pharmaceutical formulation, the kit may further include directions for the simultaneous, sequential, or separate administration of the first and second pharmaceutical compositions to a subject in need thereof.

In another embodiment, the kits are suitable for the delivery of solid oral forms of a compound of the present disclosure, such a kit includes, for example, a number of unit dosages. Such kits include card having the dosages oriented in the order of their intended use. An example of such kit is a "blister pack." Blister packs are well known in the packaging industry and are widely used for packaging pharmaceutical unit dosage forms. If desired, an aid may be provided, for example, in the form of numbers, letters, or other markings or with a calendar insert, designating the days in the treatment schedule in which the dosage can be administered.

According to one embodiment, the Kit may include, at least, (a) a first container containing any of the present compound of formula (I); and optionally, (b) a second container containing a second therapeutic agent that is any of a known anti-cancer drug; and (c) a legend associated with the kit for instructing a user how to use the kit. The legend may be in a form of pamphlet, tape, CD, VCD or DVD.

The present invention will now be described more specifically with reference to the following embodiments, which are provided for the purpose of demonstration rather than limitation. While they are typically of those that might be used, other procedures, methodologies, or techniques known to those skilled in the art may alternatively be used The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

EXAMPLES

Material and Method

Cell Culture

The tumor cell line C6/LG was derived from the C6 glioblastoma cells (Bioresource Collection and Research Center, Taiwan) expressing fusion reporter genes of luciferase and green fluorescent protein (LG). The tumor cell line C6/Lung was a subline of C6/LG cells obtained by recovery of the lung metastatic colonies that were formed when C6/LG cells were intravenously injected into the nude mice. Both cell lines were cultured in Dulbecco's modified Eagle's medium (DMEM) containing 10% fetal bovine serum (FBS) and 1% penicillin-streptomycin at 37° C. in a 5% $CO_2$ atmosphere.

Preparation of Human Platelets

The venous blood was collected from 18 to 35 year-old healthy volunteer donors (who did not take any anti-platelet medicine or other anti-inflammation medicine within two weeks before blood draw), and mixed with anti-coagulant (venous blood:anticoagulant=9:1), and then centrifuged at 200 g at RT for 15 minutes. The upper layered platelet-rich plasma (PRP) was collected, and centrifuged at 1,000 g for 10 minutes after mixing with anticoagulant (the final concentration: 0.5 μM prostacyclin and 10 U/ml heparin). The supernatant was removed, and the platelet pellets were re-suspended in Tyrode's solution and further centrifuged at 1,000 g for 10 minutes. Finally, the platelets were re-suspended in the Tyrode's solution containing calcium and magnesium ions and was termed "the wash platelet sample" in the present study. The number of platelets were calculated using the coulter counter before use, and the density of platelets was adjusted to $3 \times 10^8$ cells/ml and stored at RT until further use.

Human Platelet Aggregation Test

The platelets ($3 \times 10^8$ cells/ml) (either "the platelet-rich plasma sample" or "the wash platelet sample") was pre-heated with stir at 900 rpm at 37° C. for 1 minute, the test compound (e.g., TYZc3) was then added, and the mixture was allowed to react for 3 minutes. Additional platelet activation stimulator (e.g., collagen, U46619, thrombin and PDPN) was also added to evaluate the effect of the test compound on the platelet aggregation activation. Platelet aggregation was determined by the change in light transmission upon the aggregation of platelets using platelet aggregometer (Model 570VS, Chrono-log Corp., U.S.). Degree of platelet aggregation was calculated using the following formula:

Aggregation %=$(T_1-T_0)/(T_{b1}-T_{b0})\times 100$

In which $T_0$ and $T_1$ are transmissions of platelets respectively before and after the addition of the stimulant, $T_{b0}$ and $T_{b1}$ are transmissions of tyrode's buffer respectively before and after the addition of the stimulant.

Tumor Cell-Induced Platelet Aggregation (TCIPA)

The purified platelets ($1\times 10^9$ cells/ml) was pre-heated with stir at 900 rpm at 37° C. for 1 minute, and the compound of the present invention was added. After a 3-minute reaction, C6 tumor cells "C6-Lung" and "C6-LG" ($1\times 10^6$ cells/ml, respectively) with different levels of podoplanin (PDPN) was added to react with platelets for 15 minutes, and the change in light transmission upon the platelet aggregation were measured by platelet aggregometer.

Example 1 Synthesis of Compounds TYZc3 and TYZd1

The compounds TYZc3 and TYZ d1 were synthesized in accordance with the following Scheme I:

Briefly, N-Boc-ethylenediamine (1.0 equiv) or N-Boc-1,3-propanediamine (1.0 equiv) and benzoylchloride (1.5 equiv) were dissolved in a solvent system of pyridine (10%) and dichloromethane (DCM, 3 mL), and the mixture was allowed to react at room temperature for 8 hours. The products were then purified by silica gel chromatography and eluted with n-hexane/ethyl acetate (3:1) to afford compounds TYZ-C-A or TYZ-D-A (yield 70-80%).

Compounds TYZ-C-A or TYZ-D-A was then mixed with trifluoroacetic acid (TFA) solution (TFA/DCM=1:5) and reacted at room temperature for 4 hours. Once the reaction was completed, NaOH was added until the pH value reached 12, and then extracted by ethyl acetate (EA) to give TYZ-C-B or TYZ-D-B (yield 90-92%). Compound TYZ-C-B or TYZ-D-B was dissolved in anhydrous ACN (5 mL), then 2-amino-5-nitrobenzoic acid (1.2 equiv) and HOBt (1.5 equiv) were added, followed by the addition of 1-(3-Dimethylaminopropyl)-3-ethylcarbodiimide (EDC, 1.5 equiv). The mixture was allowed to react at room temperature for 8 hours, then subjected to purification by silica gel chromatography by eluting the column with chloroform/methanole (23:1) to afford compounds TYZ c3 or TYZ d1 (yield 35-38%).

Compound TYZ c3: $^1$H-NMR (DMSO-d6, 400 MHz) δ: 8.81 (1H, t, J=5.2 Hz NH), 8.58 (1H, t, J=5.2 Hz NH), 8.52 (1H, d, J=2.4 Hz, H'-2), 8.01 (1H, dd, J=9.2, 2.4 Hz, H'-4), 7.85 (2H, d, J=7.6 Hz, H'-8, 12), 7.74 (2H, s, $NH_2$), 7.51 (1H, t, J=7.6 Hz H'-10), 7.45 (2H, t, J=7.6 Hz, H'-9, 11), 6.79 (1H, d, J=9.2 Hz, H'-5), 3.43 (4H, quintet, J=5.6 Hz, H'-14, 15). $^{13}$C-NMR (DMSO-d6, 100 MHz) δ: 167.6 (s, C-13), 166.7 (s, C-16), 155.4 (s, C-3), 135.1 (s, C-6), 135.1 (s, C-6), 134.8 (s, C-7), 131.3 (s, C-10), 128.4 (s, C-9, 11), 127.5 (s, C-4), 126.1 (s, C-8, 12), 126.1 (s, C-2), 116.0 (s, C-5), 113.3 (s, C-1), 39.7 (m, C-14, 15).

Compound TYZ d1: $^1$H-NMR (DMSO-d6, 400 MHz) δ: 8.71 (1H, t, J=5.2 Hz, NH), 8.50 (1H, d, J=2.4 Hz, H'-2), 8.47 (1H, t, J=5.2 Hz, NH), 8.01 (1H, dd, J=9.2, 2.4 Hz, H'-4), 7.83 (2H, d, J=7.6 Hz, H'-8, 12), 7.75 (2H, s, $NH_2$), 7.51 (1H, t, J=7.6 Hz H'-10), 7.44 (2H, t, J=7.6 Hz, H'-9, 11), 6.79 (1H, d, J=9.2 Hz, H'-5), 3.31 (4H, m, J=6.4, H'-14, 16), 1.78 (2H, quintet, J=6.4, H'-15). $^{13}$C-NMR (DMSO-d6, 100 MHz) δ: 167.3 (s, C-13), 166.4 (s, C-16), 155.4 (s, C-3), 135.1 (s, C-6), 134.8 (s, C-7), 131.2 (s, C-10), 128.4 (s, C-9, 11), 127.5 (s, C-4), 127.3 (s, C-8, 12), 125.8 (s, C-2), 115.9 (s, C-5), 113.2 (s, C-1), 39.7 (m, C-14, 15, 16).

Example 2 Characterization of Compound TYZ c3

2.1 Compound TYZ c3 had No Effect on Agonist Induced Platelet Aggregation

In this example, the effect of compound TYZ c3 on agonist-induced platelet aggregation was investigated. Briefly, various platelet stimulators (e.g., collagen, thrombin, U46619) were respectively mixed with platelets in the presence or absence of compound TYX c3, and platelet aggregation were determined by platelet aggregometer as described in the "Material and "Method" section. Results are provided in FIG. 1.

Figure 1:
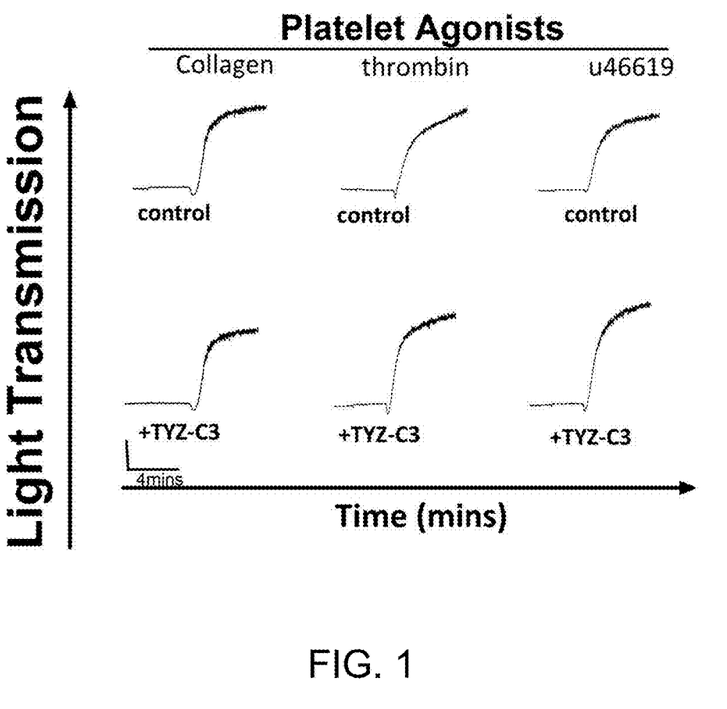
FIG. 1 depicts the effect of compound TYZ c3 on collagen-, thrombin- or U46619-induced platelet aggregation in accordance with one embodiment of the present disclosure.

As the data of FIG. 1 illustrated, collagen, thrombin, and U46619 respectively induced platelet aggregation, and such aggregation was not affected by the addition of compound TYZ c3.

2.2 Compound TYZ c3 Inhibited PDPN-Induced Tumor Cells Induced Platelet Aggregation (TCIP)

Podoplanin (PDPN), a tumor cell surface protein, is known to enhance tumor metastases by eliciting tumor cell-induced platelet aggregation (TICP). However, as depicted in FIG. 2, platelet aggregation induced by PDPN was blocked by compound TYZ c3, which suggested that compound TYZ c3 might interfere tumor metastasis.

To test the hypothesis, the effect of compound TYZ c3 was evaluated by TCIPA assay, in which tumor cells (i.e., C6 cells), instead of PDPN, were added to platelets to induce aggregation. Results are depicted in FIG. 3.

Figure 2:
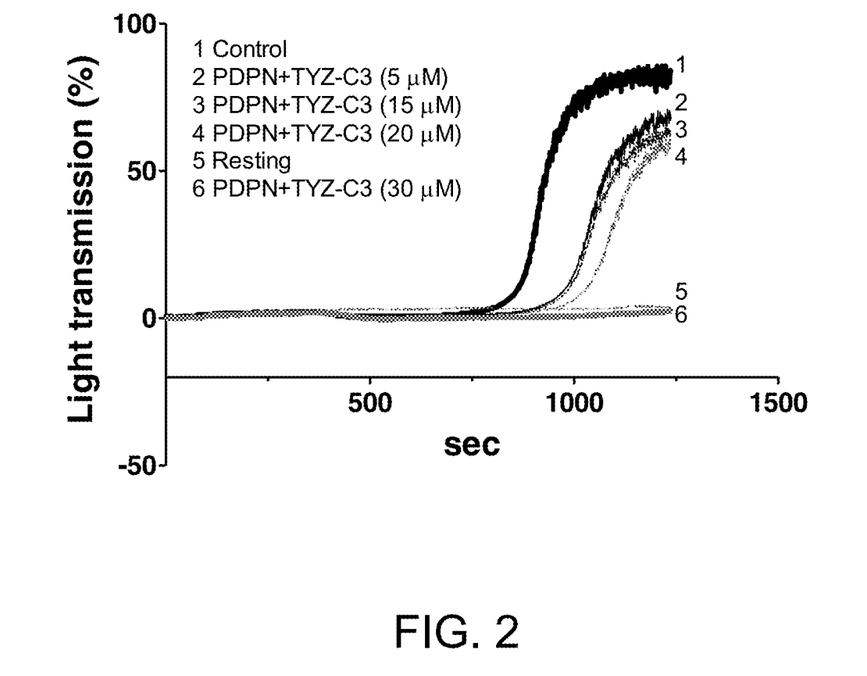
FIG. 2 depicts the effects of various concentrations of compound TYZ c3 on PDPN-induced platelet aggregation in accordance with one embodiment of the present disclosure.
Figure 3:
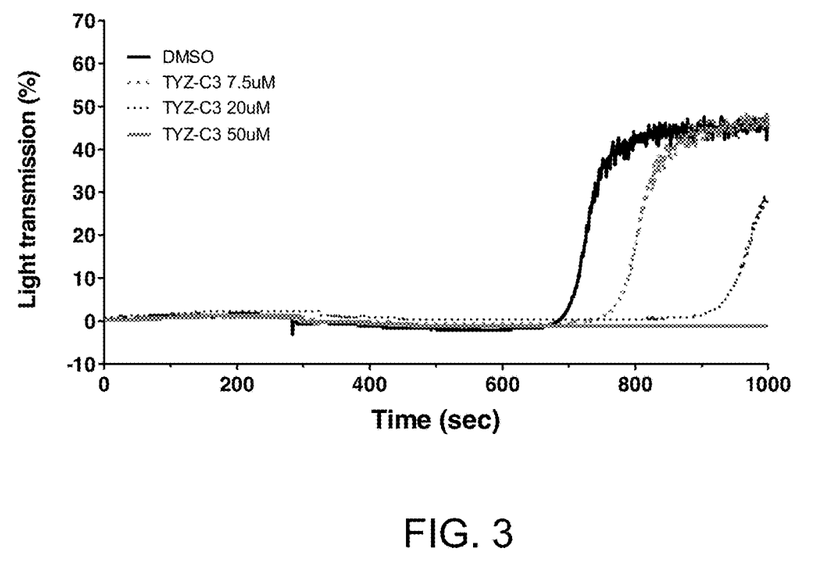
FIG. 3 depicts the effect of various concentrations of compound TYZ c3 on C6-Lung tumor cell-induced platelet aggregation in accordance with one embodiment of the present disclosure.

As illustrated in FIG. 3, platelet aggregation induced by C6 tumor cells was blocked by compound TYZ c3, consistent with the findings in FIG. 2, which support the hypothesis that compound TYZ c3 may interfere tumor metastasis, thus may serve as a lead compound for the development of a medicament for treating tumor, particularly, tumors that metastasize.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A compound of formula (I), or a pharmaceutically acceptable salt, solvate or hydrate thereof, wherein, n is 2 or 3.

2. The compound of claim 1, wherein in the formula (I), n is 2.

3. The compound of claim 2, wherein the compound is capable of suppressing tumor cells-induced platelet aggregation.

4. A pharmaceutical composition comprising an effective amount of the compound of claim 1, and a pharmaceutically acceptable carrier.

5. The pharmaceutical composition of claim 4, wherein, in the formula (I), n is 2.

* * * * *